(12) United States Patent
Farmer et al.

(10) Patent No.: US 6,538,817 B1
(45) Date of Patent: Mar. 25, 2003

(54) METHOD AND APPARATUS FOR OPTICAL COHERENCE TOMOGRAPHY WITH A MULTISPECTRAL LASER SOURCE

(75) Inventors: Jason N. Farmer, Kenmore, WA (US); Charles I. Miyake, Kirkland, WA (US)

(73) Assignee: Aculight Corporation, Bothell, WA (US)

( * ) Notice: Subject to any disclaimer, the term of this patent is extended or adjusted under 35 U.S.C. 154(b) by 0 days.

(21) Appl. No.: 09/690,562

(22) Filed: Oct. 17, 2000

Related U.S. Application Data
(60) Provisional application No. 60/161,470, filed on Oct. 25, 1999.

(51) Int. Cl.⁷ .............................................. G02B 27/10
(52) U.S. Cl. ..................................................... 359/618
(58) Field of Search ................................ 359/618, 629, 359/641; 372/4

(56) References Cited

U.S. PATENT DOCUMENTS

| | | | |
|---|---|---|---|
| 4,494,235 A | 1/1985 | Guch, Jr. et al. | 372/23 |
| 4,913,525 A | 4/1990 | Asakura et al. | 350/162.12 |
| 4,923,270 A | 5/1990 | Carter | 350/96.18 |
| 5,007,698 A | 4/1991 | Sasaki et al. | 350/96.15 |
| 5,052,013 A | 9/1991 | Putnam | 372/97 |
| 5,115,444 A | 5/1992 | Kirkby et al. | 372/50 |
| 5,136,420 A | 8/1992 | Inagaki et al. | 359/341 |
| 5,163,058 A | 11/1992 | Farries et al. | 372/6 |
| 5,276,695 A | 1/1994 | Scheps | 372/20 |
| 5,351,262 A | 9/1994 | Poguntke et al. | 372/102 |
| 5,386,426 A | 1/1995 | Stephens | 372/20 |
| 5,390,201 A | 2/1995 | Tomono et al. | 372/22 |
| 5,450,232 A | 9/1995 | Sasaki et al. | 359/341 |
| 5,513,201 A | 4/1996 | Yamaguchi et al. | 372/75 |
| 5,541,946 A | 7/1996 | Scheps et al. | 372/23 |
| 5,633,718 A * | 5/1997 | Manning | 356/4.01 |
| 5,773,345 A | 6/1998 | Ota | 438/286 |
| 5,802,092 A | 9/1998 | Endriz | 372/50 |

FOREIGN PATENT DOCUMENTS

| | | | |
|---|---|---|---|
| EP | 0 440 485 A2 | 1/1991 | G02B/6/34 |

OTHER PUBLICATIONS

M.C. Farries et al., Electronics Letters, Aug. 15, 1991, vol. 27, No. 17, pp. 1498–1499.

(List continued on next page.)

*Primary Examiner*—Ricky Mack
(74) *Attorney, Agent, or Firm*—Bingham McCutchen, LLP; David G. Beck

(57) ABSTRACT

A method and apparatus for performing optical coherence tomography using a wavelength multiplexed source is provided. The single output beam of the source is of a large bandwidth, thus providing a high resolution tomography system. In order to achieve high contrast as well, the wavelength multiplexed source has minimal wavelength separation between spectrally adjacent lasers and has an output beam with an approximately Gaussian spectral shape. The source is preferably comprised of one or more multi-gain element arrays multiplexed together within a single external resonator cavity. Interposed between the array and the resonator cavity output coupler are a collimating element and a diffraction grating. The collimating element can be a refractive optic, a reflective optic, or, for some applications, a ¼ pitch GRIN lens. The diffraction grating can either be transmissive or reflective. The combination of the diffraction grating and the collimating element forces each emitter within the array to lase at a distinct wavelength. In order to achieve an overall bandwidth greater than the gain bandwidth of a single emitter array, either multiple arrays of differing center wavelength are packaged together or a large array is used with a laterally varying quantum well thickness or epitaxy. An intracavity spatial filter can be used to improve the beam quality and reduce cross-talk. An optical coherence tomography imaging system is coupled to the resonator cavity.

50 Claims, 6 Drawing Sheets

OTHER PUBLICATIONS

J.B.D. Soole et al., Electronics Letters, Sep. 10, 1992, vol. 28, No. 19, pp. 1805–1807.

J.B.D. Soole et al., Appl. Phys. Lett. 61(23), Dec. 7, 1992, pp. 2750–2752.

J.B.D. Soole et al., Appl. Phys. Lett. 58(18), May 6, 1991, pp. 1949–1951.

B. Bouma et al., Optics Letters, vol. 20, No. 13, Jul. 1, 1995, pp. 1486–1488.

J.G. Fujimoto et al., Annals New York Academy of Sciences, *New Technology for High–Speed and High–Resolution Optical Coherence Tomography*, pp. 95–107, Feb. 9, 1998.

J.G. Fujimoto et al., Nature Medicine, vol. 1, No. 9, 9/95, pp. 970–972.

G.J. Tearney et al., Optics Letters, vol. 21, No. 17, Sep. 1, 1996, pp. 1408–1410.

\* cited by examiner

METHOD AND APPARATUS FOR OPTICAL COHERENCE TOMOGRAPHY WITH A MULTISPECTRAL LASER SOURCE

CROSS-REFERENCES TO RELATED APPLICATIONS

This application claims priority of provisional patent application Serial No. 60/161,470 filed Oct. 25, 1999, the disclosure of which is incorporated herein by reference for all purposes.

GOVERNMENT RIGHTS NOTICE

This invention was made with Government support under Contract No. F29601-98-C-0181 awarded by the Air Force. The Government has certain rights in the invention.

FIELD OF THE INVENTION

The present invention relates generally to optical systems and, more particularly, to a method and apparatus for performing optical coherence tomography.

BACKGROUND OF THE INVENTION

Optical coherence tomography or OCT is an imaging technique used to provide cross-sectional images of biological systems. OCT has been used to diagnose and monitor ocular diseases such as glaucoma and macular edema and, to the extent permissible by optical attenuation, image non-transparent tissues. In vitro OCT has also found applications in arterial pathology, gastroenterology, urology, and neurosurgery. An advantage of OCT over ultrasound imaging is its ability to achieve spatial resolutions of 10 micrometers or less, approximately 10 times better than that offered by ultrasound.

In operation, a beam of light is focussed on the tissue to be imaged and the tissue reflectivity as a function of depth is measured using a scanning interferometer. By scanning the light beam in a transverse direction, a cross-sectional image is constructed. As the axial resolution is directly proportional to the coherence length of the light source, and the coherence length is inversely proportional to the spectral bandwidth, typically either mode-locked lasers or semiconductor sources with a chirped quantum well structure are used. For example, OCT using a Kerr-lens mode-locked Ti:Al$_2$O$_3$ laser is described in an article by Bouma et al. entitled *High-Resolution Optical Coherence Tomographic Imaging Using a Mode-Locked Ti:Al$_2$O$_3$ Laser Source* published in Optics Letters, Vol. 20, No. 13, Jul. 1, 1995.

Conventional OCT light sources suffer from various limitations. Chirped semiconductor lasers used in these systems often have inadequate brightness to achieve the desired OCT image contrast and frequently provide too little bandwidth to achieve the desired resolution. Alternative sources based on mode-locked solid state lasers are large, costly, and can require frequent adjustment. Furthermore, due to the bandwidth inflexibility of the employed sources, an OCT system designed for one type of biological tissue may not be optimal for another type of biological tissue. Accordingly, what is needed in the art is a low cost, compact OCT system utilizing a high brightness source with a large, preferably adjustable, bandwidth. The present invention provides such a system.

SUMMARY OF THE INVENTION

The present invention provides a method and apparatus for performing optical coherence tomography using a wavelength multiplexed source in which the single output beam is of a large bandwidth. As a result of the large bandwidth, the tomography system achieves very high resolution, thus allowing cellular structures to be resolved. In order to achieve high contrast as well, the wavelength multiplexed source has minimal wavelength separation between spectrally adjacent lasers and has an output beam with an approximately Gaussian spectral shape.

In at least one embodiment of the invention, a multi-gain element array is used within an external resonator. Interposed between the array and the resonator output coupler are a collimating element and a diffraction grating. Typically either a refractive optic or a reflective optic is used as the collimating element although for some applications a ¼ pitch GRIN lens can be used. The diffraction grating can either be transmissive or reflective. The combination of the diffraction grating and the collimating element forces each emitter within the array to lase at a distinct wavelength. Since the gain bandwidth of a single emitter array is typically less than the desired bandwidth, either multiple arrays of differing center wavelength are packaged together or a large array is used with a laterally varying quantum well thickness or epitaxy. An intracavity spatial filter can be used to improve the beam quality and reduce cross-talk. External to the resonator cavity is an optical delivery system for transmitting the optical energy to the area to be imaged. If necessary, the spectral profile of the output beam can be improved using a dielectric filter. Alternately, the spectral profile of the output beam can be modified using a second diffraction grating and an additional optical element interposed between the resonator cavity and the optical delivery system. The grating redisperses the light in the output beam while the additional optical element reshapes the profile as desired.

In at least another embodiment of the invention, the outputs of a pair of multiple gain elements arrays are multiplexed within a single resonator cavity, the resonator cavity being comprised of a high reflector, preferably applied to the back facets of the arrays, and an output coupler. Multiplexing can be achieved, for example, with a polarization sensitive beam combiner. Interposed between each array and the output coupler are a collimating optic and a single diffraction grating, both of which can either be transmissive or reflective. The combination of the diffraction grating and the collimating element forces each emitter within each array to lase at a distinct wavelength. Each of the arrays are positioned relative to one another and to the diffraction grating in such a manner as to cause an interlacing of the lasing wavelengths of the individual gain elements of the two arrays. As a consequence, the wavelength separation between spectrally adjacent lasers is further reduced, thus achieving further improvement in image contrast. Each array can be comprised of multiple arrays of differing center wavelength packaged together or of a single, large array with a laterally varying quantum well thickness or epitaxy. An intracavity spatial filter can be used to improve the beam quality and reduce cross-talk. External to the resonator cavity is an optical delivery system for transmitting the optical energy to the area to be imaged. In order to improve the spectral profile of the output beam, either an optical filter or the combination of a second diffraction grating and an additional optical element can be interposed between the resonator cavity and the optical delivery system.

A further understanding of the nature and advantages of the present invention may be realized by reference to the remaining portions of the specification and the drawings.

DESCRIPTION OF THE SPECIFIC EMBODIMENTS

Figure 1:
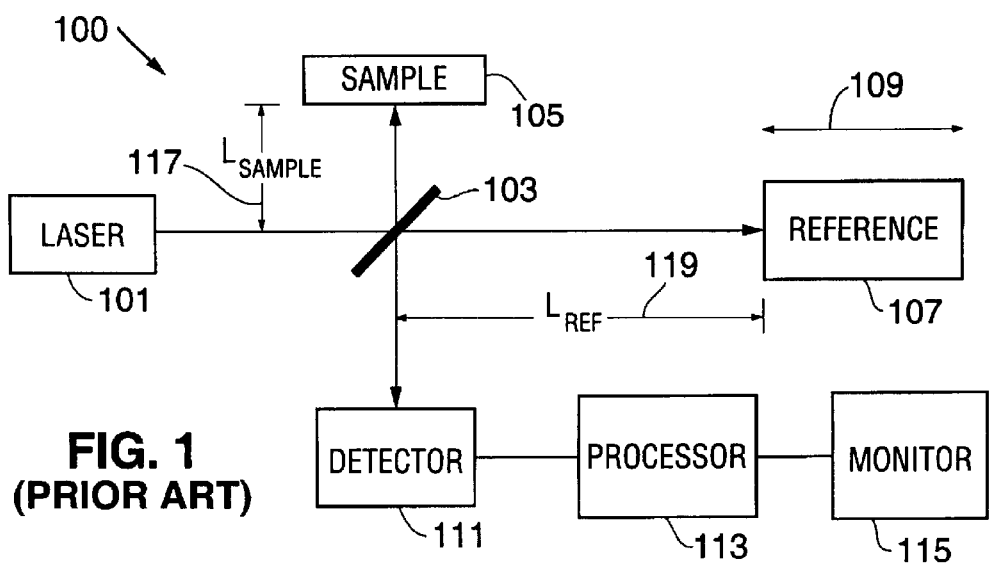
FIG. 1 schematically illustrates the principles of an OCT system.

FIG. 1 schematically illustrates the principles of an OCT system. As shown, the basic OCT system 100 uses a Michelson type interferometer with a laser source 101 as the light source. The light from source 101 is split with mirror 103, one portion of the light impinging on a sample 105 and the other portion of the light impinging on a reference mirror 107. Reference mirror 107 is mounted to a translation stage (not shown) that allows the distance separating reference 107 and beam splitter 103 to be varied along an axis 109. The light reflected by sample 105 and reference 107 is received by a detector 111. The signals from detector 111 are processed by a processor 113. Preferably a monitor 115 is used to display the OCT image.

The light intensity at detector 111 is dependent on both the amplitude and the phase of the received light. The amplitude of the reflected sample wave is proportional to the reflectivity of sample 105. The phase difference between the reference and sample waves is proportional to the optical path length difference of the two arms, i.e., distances 117 and 119. Translating reference 107 along axis 109 changes the path length difference, thus changing the relative phases of the two waves. As a result, the interference effects cause oscillations in the intensity received by detector 111.

The sinusoidal oscillations at detector 111 are only present when the optical path length difference between the two arms, i.e., $L_{ref}$ 119–$L_{sample}$ 117, is less than the coherence length of the laser source. Once the path length difference exceeds the coherence length, the interference effects are washed out. As a consequence, high resolution OCT imaging relies upon a laser source with a very short coherence length.

Assuming a Gaussian spectral profile, the coherence length, and thus the OCT system resolution, is given by $$\Delta z = \frac{2 \ln 2}{\pi} \frac{\lambda^2}{\Delta \lambda},$$

where $\Delta z$ is the coherence length, $\lambda$ is the wavelength, and $\Delta \lambda$ is the bandwidth. For spectrally non-Gaussian sources, however, the formula given above is only approximate. Analysis of the Michelson type interferometer shows that for a fixed sample, the detector signal and the laser source spectrum are mathematically related to one another through an inverse Fourier transform. The Fourier transform can be approximately viewed as the point spread function of the OCT imaging system, hereafter referred to as the fringe visibility function. The resulting OCT image is then a convolution of the reflectivity profile of the sample with the fringe visibility function. Hence, the fringe visibility function defines both the image resolution and image contrast. Specifically, resolution is defined by the width of the central peak of the fringe visibility function which is proportional to the width of the spectrum. Thus high resolution OCT requires a broad bandwidth source. Contrast, which describes the ability of the OCT system to distinguish high reflectivity tissue from adjacent low reflectivity tissue, is defined by the amplitude of the fringe visibility function away from its central peak. Therefore the best spectral profile is Gaussian in nature.

Figure 2:
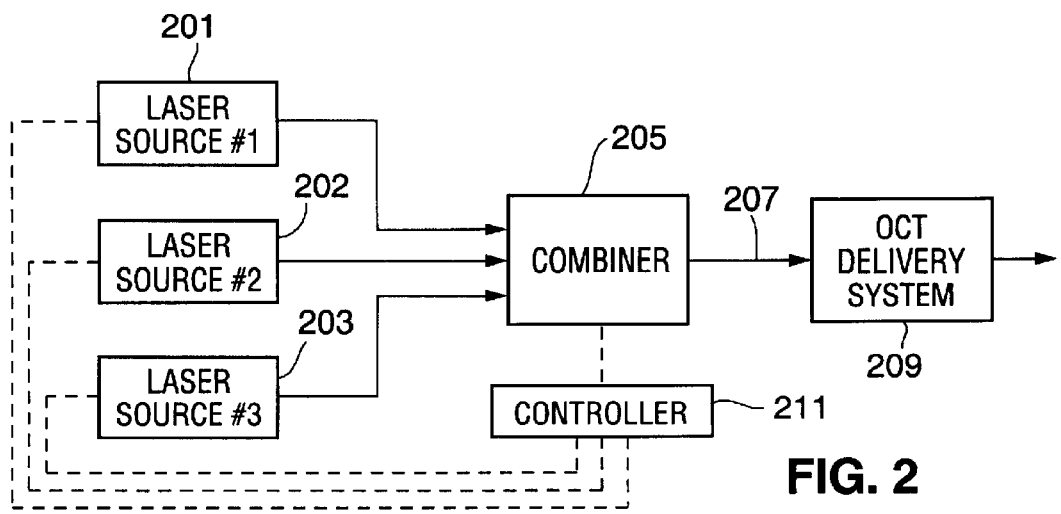
FIG. 2 schematically represents the invention.

FIG. 2 is a schematic representation of the invention. As shown, the outputs from multiple sources 201–203 are combined with a beam combining system 205, yielding an output beam 207 of the desired bandwidth and spectral shape. As discussed further below, preferably the wavelength separation between spectrally adjacent lasers is minimized. It is understood that the use of three laser sources 201–203 is meant to be illustrative, not limiting, of the present invention. As discussed below, preferably the present invention utilizes at least 10 laser sources, more preferably at least 50 laser sources, more preferably still at least 100 laser sources, and more preferably still 500 or more laser sources. An optical delivery system 209 splits off a portion of output beam 207 as a reference beam prior to transmitting the sample beam to the tissue or area to be imaged. Delivery system 209 uses optical fibers, optical elements, or a combination thereof As the design of OCT imaging systems such as that shown in FIG. 1 are well known by those of skill in the art, further discussion of delivery system 209 is not included herewith. Preferably a controller 211 is coupled to sources 201–203 and combiner 205, controller 211 controlling the center wavelength, bandwidth, and spectral shape of the system.

Figure 3:
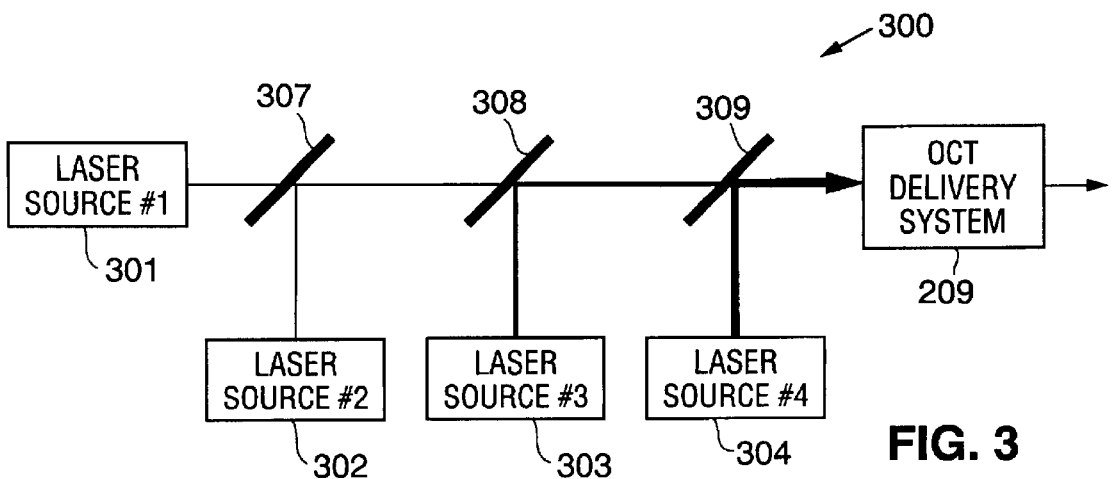
FIG. 3 is an illustration of an OCT laser system utilizing a plurality of individual laser sources.

FIG. 3 is an illustration of a system 300 in accordance with the invention. As shown, a plurality of laser sources 301–304 are combined into a single beam 305 using beam combining elements 307–309. Beam combining elements 307–309 are optical beam combiners which utilize dichroic filters designed through the application of well known coating design techniques. For example, filter 309 is designed to pass the wavelength bands generated by sources 301–303 while reflecting the wavelength band spectrum generated by source 304.

In the preferred embodiment of the present invention, one or more multiple element arrays, e.g., index guided diode arrays, and a grating or other beam combiner are used to achieve a broad bandwidth, multi-spectral OCT source. An advantage of building up the spectral width using individual elements is that the total bandwidth, and thus the axial image resolution, can be engineered to meet the requirements of the user. Additionally, the technique of the present invention increases the brightness of the source by forcing the beams from all of the individual emitters to be collinear, thereby enhancing the OCT image contrast and decreasing the time required to take an individual image.

In order to achieve the desired image contrast and resolution, the three primary areas to consider are (i) the total bandwidth of all of the individual lasers, (ii) the overall spectral shape of the output radiation, and (iii) the wavelength separation between spectrally adjacent lasers. Fortunately, each of these three design issues can be addressed and optimized separately. In general terms, the highest resolution is achieved by maximizing the total bandwidth of all of the individual lasers while the best contrast is achieved by minimizing the wavelength shift between spectrally adjacent lasers and forcing the overall spectrum to resemble, as closely as possible, a Gaussian.

Maximizing the total bandwidth of an OCT imaging system based upon the present invention can be achieved by wavelength multiplexing one or more laser arrays. For example, diode lasers are commercially available with operational wavelengths between 650 and 2000 nanometers. Therefore wavelength multiplexing many of these together would result in a very high resolution OCT imaging system. However, indiscriminately adding bandwidth to a laser source, while yielding high resolution, can also lead to a system with very low contrast, thus preventing a clear distinction between different tissue types and potentially hiding low reflectivity features that lie in proximity to higher reflectivity ones. This phenomena is due to the additional spatial frequency components in the fringe visibility function that arise from any spectral ripple.

OCT image contrast, besides being dependent upon the wavelength shift between spectrally adjacent lasers and the overall spectrum shape, is also dependent upon the scattering and absorption properties of the constituents of the tissue sample under examination. For example, melanin and connective tissue are more highly scattering than adipose or muscle. Thus, even with an OCT system using a Gaussian source with less than 100 nanometers of bandwidth, the achievable contrast between tissue constituents is determined by the differences in optical properties of the tissue near the center wavelength of the source. Therefore an OCT system based on the present invention which allows imaging at more than one center wavelength can be used to yield improved contrast by taking advantage of the intrinsic wavelength dependence of the optical properties of tissue.

Figure 4:
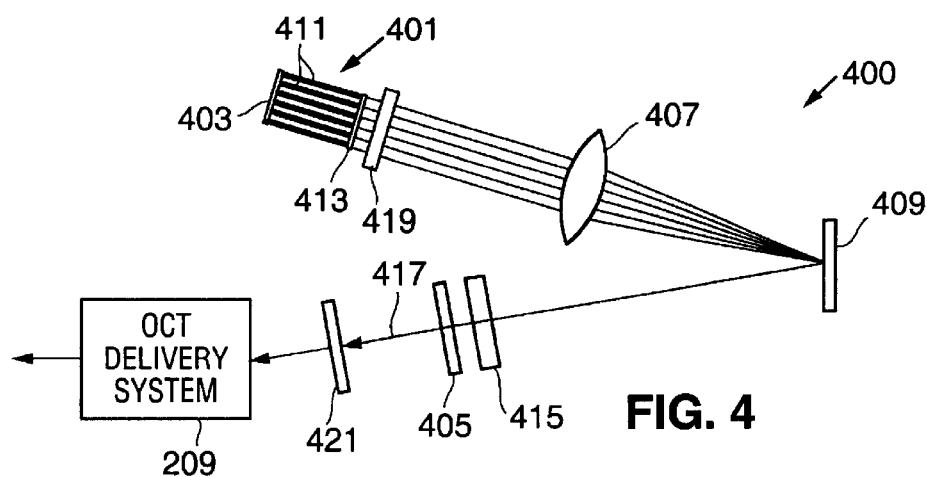
FIG. 4 is an illustration of an OCT laser system utilizing a multi-element array, an intracavity transmissive collimating optical element, and an intracavity reflective diffraction grating.

FIG. 4 schematically illustrates a laser system 400 in accordance with the invention. It is understood that FIG. 4 is not an accurate ray tracing schematic, but is merely intended to represent the relationship of the various elements of system 400. Laser system 400 includes a laser gain element array 401 utilizing an external resonator, the resonator cavity comprised of a reflector 403, preferably a high reflection coating applied to the back facets of array 401, and an output coupler 405. Interposed between the array and output coupler 405 are a collimating lens 407 and a diffraction grating 409. External to the resonator cavity is the OCT delivery system 209 which, as previously discussed, can be comprised of either refractive or reflective optical elements or both, and typically uses one or more optical fibers as a means of delivering the optical energy to the area to be imaged.

Collimating lens 407 serves two purposes. First, lens 407 collimates the light from individual gain elements 411. Second, lens 407 causes the light from individual gain elements 411 to be spatially overlapped onto diffraction grating 409, assuming that the distance separating grating 409 from lens 407 is equal to or greater than the focal length of element 407. In the preferred embodiment, the distance separating grating 409 and lens 407 is substantially equivalent to the focal length of lens 407 as is the distance separating array 401 from lens 407.

Due to the disclosed laser system configuration in which the feedback path of the individual emitters includes the combination of diffraction grating 409 and lens 407, each emitter in array 401 is forced to lase at a distinct wavelength. The wavelength at which each emitter is forced to lase is determined by the grating equation, the cavity geometry, and the emitter structure of array 401. The grating equation is given by:

$$\mathrm{Sin}(\theta_{incident} + n\Delta\theta) + \mathrm{Sin}(\theta_{out}) = \frac{m\lambda_n}{d},$$

where $\lambda_n$ is the wavelength of the $n^{th}$ emitter of array 401, m the diffraction order, d the grating ruled spacing, $\theta_{incident}$ the incident angle of each beam at the grating, and $\theta_{out}$ the common output angle for each beam. The wavelength shift required between each adjacent emitter 411 is then $$\Delta\lambda = \frac{sd\mathrm{Cos}(\theta_{incident})}{f},$$

where s is the separation between emitters and $f$ is the focal length of intracavity lens 407.

It is understood that active elements 411 can either be single mode or multi-mode gain elements. The benefit of using multi-mode gain elements is that a flatter emission spectrum is typically easier to achieve than it is using single transverse mode elements due to the improved fill factor associated with the multi-mode elements. Array 401 can be comprised of a semiconductor diode laser array, a stack of side or end pumped solid state laser materials, or a fiber laser array. Suitable solid state laser materials include, but are not limited to, alexandrite, $CO:MgF_2$, and Cr:LiSAF.

Since the physical spacing between emitters controls the wavelength shift between adjacent emitters, one of the primary considerations in selecting the emitters comprising array 401 is the emitter spacing. Specifically, array 401 is selected to achieve very closely spaced emitters. One technique for achieving extremely close emitter spacing is to use index guided arrays, i.e., arrays in which individual emitters are optically isolated from one another using a boxcar lateral index profile. In addition to considering emitter spacing, the overall bandwidth is critical as it determines the achievable resolution of the OCT system. Since the gain bandwidth of a single emitter array is typically less than the desired bandwidth, several techniques can be used to achieve the desired bandwidth. For example, a large number of individual arrays can be packaged together, each individual array having a distinct center wavelength. Alternately, a large array can be used with a laterally varying quantum well thickness or epitaxy, thus achieving a wavelength gradient across the array.

In the preferred embodiment, an anti-reflection (i.e., AR) coating is applied to front facets 413 of array 401. AR coating facets 413 reduces the optical losses within system 400.

In the preferred embodiment of the invention, laser system 400 includes a spatial filter 415 in order to improve beam quality and reduce cross-talk. Preferably spatial filter 415 is interposed between grating 409 and output coupler 405. For example, spatial filter 415 can be comprised of an aperture or a combination of an aperture and a lens, the aperture located at the image plane of the gain elements. Preferably the aperture of spatial filter 415 is smaller than the image of an individual gain element, thus improving the beam quality of emitted beam 417. If the aperture size is sufficiently small, the beam quality will approach the diffraction limit.

In another alternate embodiment, laser system 400 includes an additional optical element 419 positioned adjacent to the emitting facets of array 401. Preferably optical element 419 is comprised of a plurality of microlenses such that there is an individual microlens which corresponds to each active element 411. Due to the rapidly diverging, astigmatic nature of the emissions from active elements 411, optical element 419 can be used to reduce the divergence, thus allowing a reduction in the size of the optics which follow element 419, e.g., lens 407. In addition, laser system 400 is less aberration sensitive due to the inclusion of optical element 419.

In another alternate embodiment, laser system 400 includes an additional optical element 421 located outside of the resonator cavity and prior to OCT delivery system 209. Optical element 421 is used to tailor the spectral profile input into the delivery system by the laser system. Typically a dielectric filter is used for optical element 421, the filter being suitably coated to provide the desired variation in transmissivity. Alternately, the combination of a grating and an optical filter can be used to reshape the optical spectrum as desired, the grating dispersing the light in beam 417 and the optical filter, characterized by a lateral variation in transmissivity, reshaping the spectrum.

Figure 5:
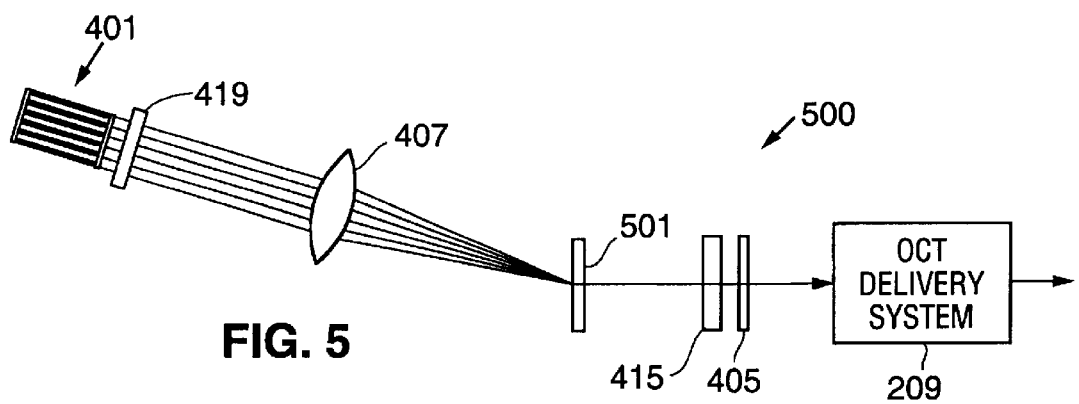
FIG. 5 is an illustration of an OCT laser system utilizing a multi-element array, an intracavity transmissive collimating optical element, and an intracavity transmissive diffraction grating.
Figure 6:
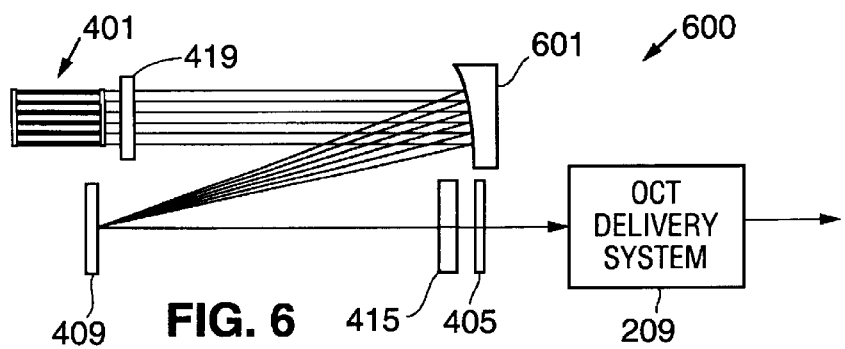
FIG. 6 is an illustration of an OCT laser system utilizing a multi-element array, an intracavity reflective collimating optical element, and an intracavity reflective diffraction grating.
Figure 7:
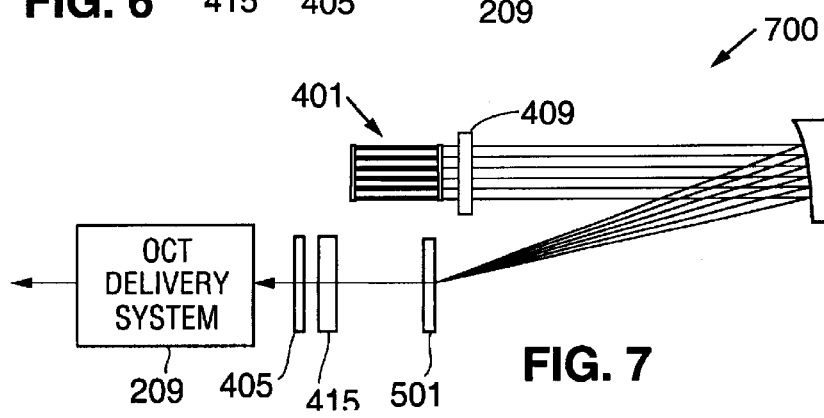
FIG. 7 is an illustration of an OCT laser system utilizing a multi-element array, an intracavity reflective collimating optical element, and an intracavity transmissive diffraction grating.
Figure 8:
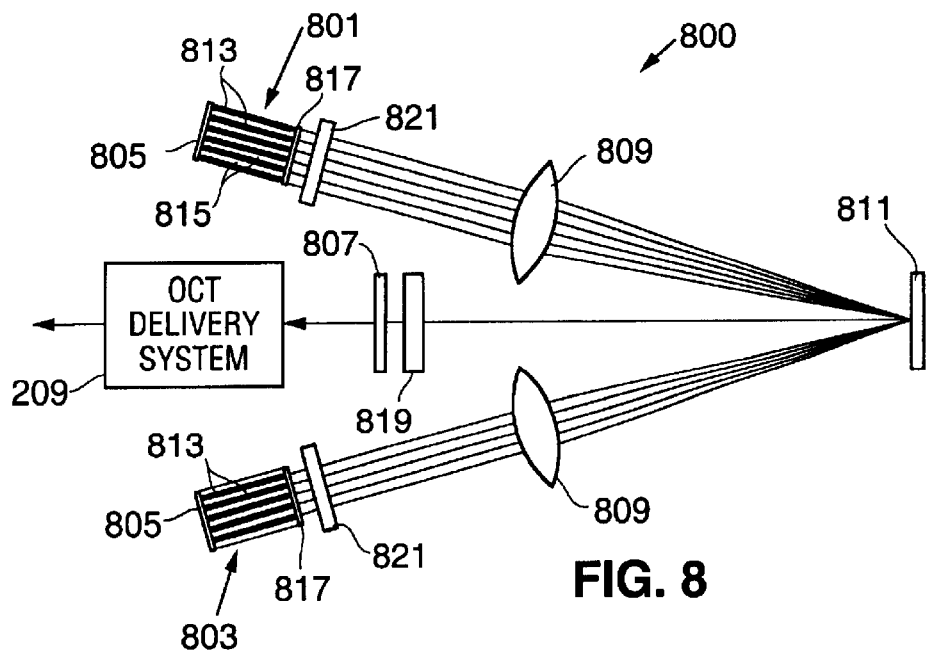
FIG. 8 is an illustration of an OCT laser system utilizing a pair of multi-element arrays, a pair of intracavity transmissive collimating optical elements, and an intracavity reflective diffraction grating.
Figure 9:
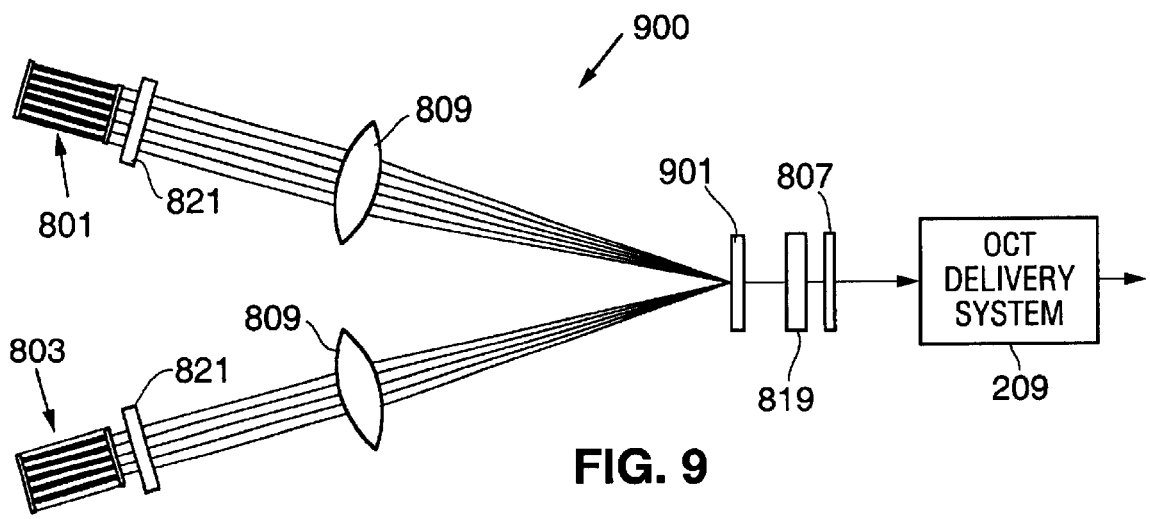
FIG. 9 is an illustration of an OCT laser system utilizing a pair of multi-element arrays, a pair of intracavity transmissive collimating optical elements, and an intracavity transmissive diffraction grating.
Figure 10:
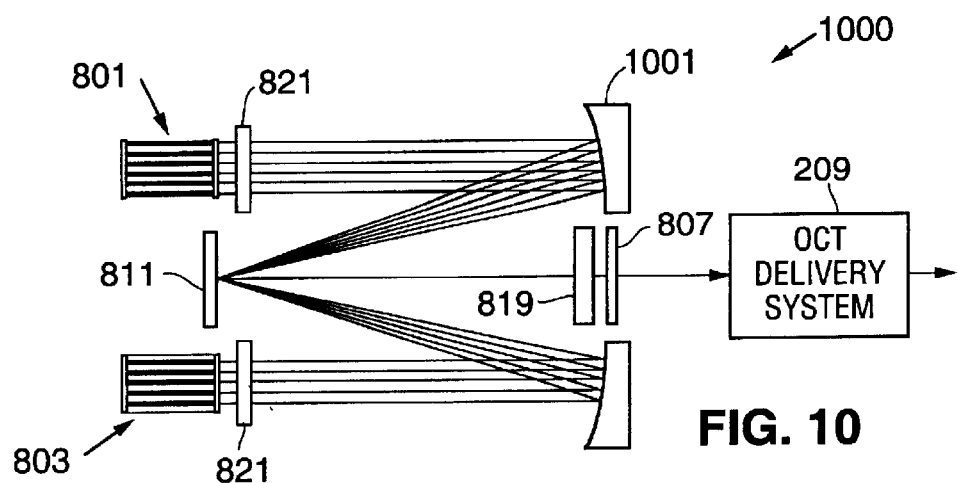
FIG. 10 is an illustration of an OCT laser system utilizing a pair of multi-element arrays, a pair of intracavity reflective collimating optical elements, and an intracavity reflective diffraction grating.
Figure 11:
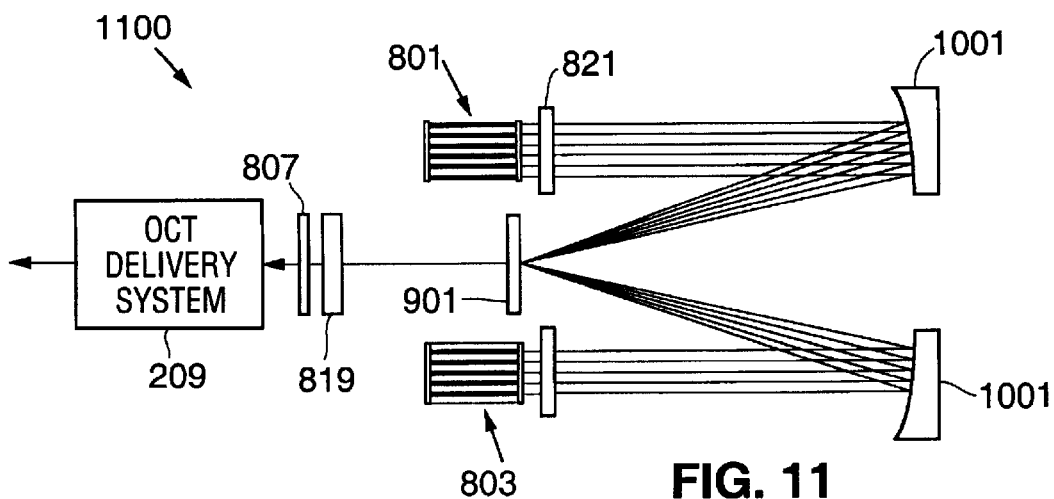
FIG. 11 is an illustration of an OCT laser system utilizing a pair of multi-element arrays, a pair of intracavity reflective collimating optical elements, and an intracavity transmissive diffraction grating.

FIGS. 5–7 illustrate other embodiments of the invention. Specifically, systems 500–700 are identical to system 400 except system 500 utilizes a transmissive diffraction grating 501; system 600 utilizes a reflective collimating optic 601; and system 700 utilizes both transmissive grating 501 and reflective collimating optic 601. Although not shown, each of these embodiments can also be configured to utilize external laser cavity optical elements (e.g., element 421) to shape and/or condition the laser system output.

FIGS. 8–11 illustrate a technique for achieving closer emitter spacing than that achievable with systems 400–700. In each of the illustrated systems, the outputs from a pair of gain element arrays 801 and 803 are combined utilizing a single external resonator cavity, the resonator cavity being comprised of a reflector 805, preferably a high reflection coating applied to the back facets of arrays 801 and 803, and an output coupler 807. Interposed between each array and output coupler 807 are a collimating optic and a single diffraction grating. The collimating optic can either be refractive, e.g., optic 809, or reflective, e.g., optic 1001. Similarly, the diffraction grating can either be reflective, e.g., grating 811, or transmissive, e.g., grating 901.

Preferably, arrays 801 and 803 each have a 50 percent duty cycle. In other words, the widths associated with active gain elements 813 are substantially equivalent to the widths associated with the non-active, i.e., non-light emitting regions 815. Array 801 is positioned relative to diffraction grating 811, and preferably to the positive first order of diffraction grating 811, such that a first active element resonates wavelengths from $\lambda$ to $\lambda+\Delta\lambda$, a second active element resonates wavelengths from $\lambda+2\Delta\lambda$ to $\lambda+3\Delta\lambda$, and a $n^{th}$ element resonates wavelengths from $\lambda+(2n-2)\Delta\lambda$ to $\lambda+(2n-1)\Delta\lambda$. In order to achieve a substantially continuous output wavelength spectrum, array 803 is positioned relative to diffraction grating 811, and preferably to the negative first order of diffraction grating 811, such that a first active element resonates wavelengths from $\lambda+\Delta\lambda$ to $\lambda+2\Delta\lambda$, a second active element resonates wavelengths from $\lambda+3\Delta\lambda$ to $\lambda+4\Delta\lambda$, and a $n^{th}$ element resonates wavelengths from $\lambda+(2n-1)\Delta\lambda$ to $\lambda+(2n)\Delta\lambda$. As a result, the output spectrum of system 800 is substantially spectrally continuous from $\lambda$ to $\lambda+(2n)\Delta\lambda$.

It is understood that although preferably the arrays utilize 50 percent duty cycles, other duty cycles can be utilized. For example, array 801 can utilize a 20 percent duty cycle and array 803 can utilize an 80 percent duty cycle. By offsetting the two arrays relative to the diffraction grating, 20 percent of the system's continuous spectrum will be generated by one array with the remaining 80 percent generated by the second array. Other complementary duty cycles can also be used.

As in the embodiments shown in FIGS. 4–7, systems 800–1100 include OCT delivery system 209. Additionally, and as previously discussed, preferably each of these systems also includes an AR coating 817 on the front facets of arrays 801 and 803, a spatial filter 819 interposed between the diffraction grating and output coupler 807, and a microlens array 821 interposed between each of the arrays and the corresponding collimating optics. Furthermore, each of these embodiments can also be configured to utilize external laser cavity optical elements to shape and/or condition the output spectrum.

Figure 12:
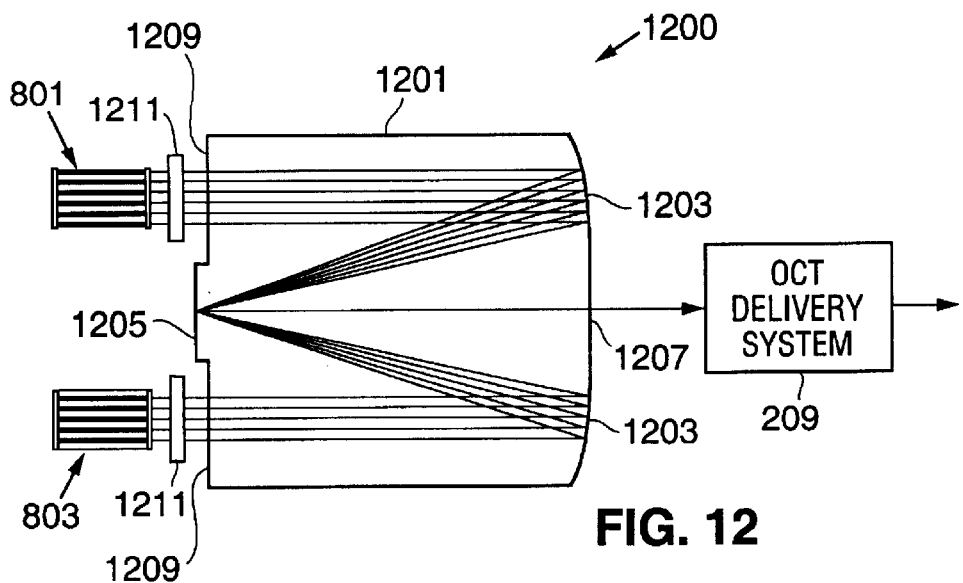
FIG. 12 is an illustration of an OCT laser system utilizing a pair of multi-element arrays and a monolithic cavity design.

FIG. 12 is an illustration of an alternate laser system 1200 that is similar to system 1000 except for the use of a monolithic cavity design. Preferably monolithic element 1201 is comprised of a single material which is substantially transparent to the wavelengths of interest. After shaping, a reflective coating is applied to surfaces 1203, resulting in a mirrored surface that collimates the light from the individual array gain elements. Monolithic element 1201 also includes a reflective diffraction grating 1205 which can be fabricated onto the desired surface of element 1201 using any of a variety of known techniques. A suitable partially reflective coating is applied to surface 1207, this surface acting as the output coupler of the resonator cavity. In order to minimize optical losses of laser system 1200, preferably surfaces 1209 are AR coated.

In the preferred embodiment of laser system 1200, arrays 801 and 803 are bonded to monolithic element 1201 using an optically transparent adhesive, thus achieving a very robust optical system. If desired, an optical element such as a microlens array 1211 can be interposed between arrays 801 and 803 and monolithic element 1201. Although microlens array 1211 can be ground into the surface of monolithic element 1201, preferably element 1211 is separately fabricated and then bonded to element 1201 using optically transparent adhesive.

FIGS. 13–16 illustrate a variety of embodiments of the invention which utilize a beam combining element 1301. Due to the use of element 1301, these embodiments do not utilize both the positive and negative orders of the grating, thus reducing cross-talk. As illustrated, the emissions from arrays 801 and 803 are combined using beam combining element 1301 prior to collimating the emissions onto the grating. Preferably beam combining element 1301 is a polarization sensitive beam combiner, such as a thin film polarizer. The output from one array, e.g., array 801 in FIGS. 13–16, passes through a wave plate 1303 prior to impinging on the polarization sensitive beam combiner 1301. As a consequence, the output of array 801 is reflected by element 1301 while the output from array 803 is transmitted by element 1301. Either a reflective element 1305 or a transmissive element 1401 collimates the array emissions onto the diffraction grating. Depending upon the desired configuration, the diffraction grating can either be reflective, as in grating 1307, or transmissive, as in grating 1403. As previously described, the embodiments shown in FIGS. 13–16 can include spatial filter 819 and/or beam conditioning optics 821 (not shown). Lastly, as shown and described with relation to FIG. 4, each of these embodiments can also be configured to utilize external laser cavity optical elements to shape and/or condition the output spectrum.

Figure 13:
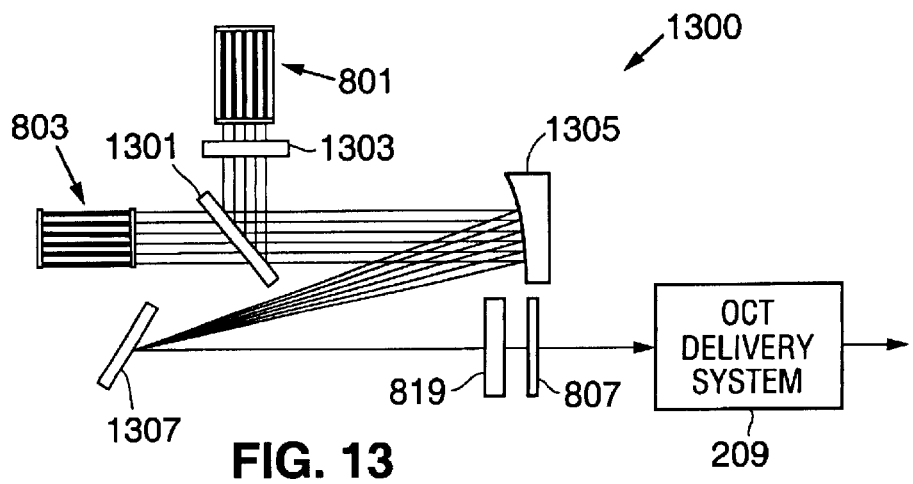
FIG. 13 is an illustration of an OCT laser system utilizing polarization multiplexing, a reflective collimating element, and a reflective diffraction grating.
Figure 14:
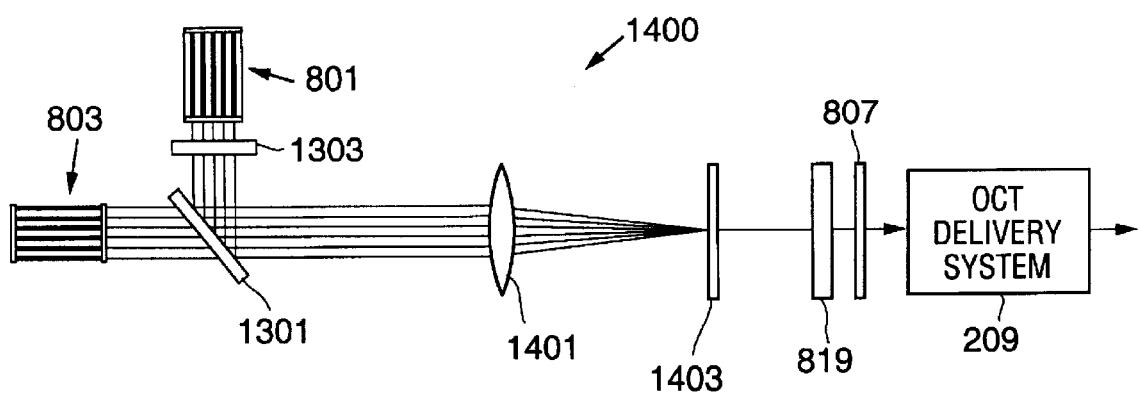
FIG. 14 is an illustration of an OCT laser system utilizing polarization multiplexing, a transmissive collimating element, and a transmissive diffraction grating.
Figure 15:
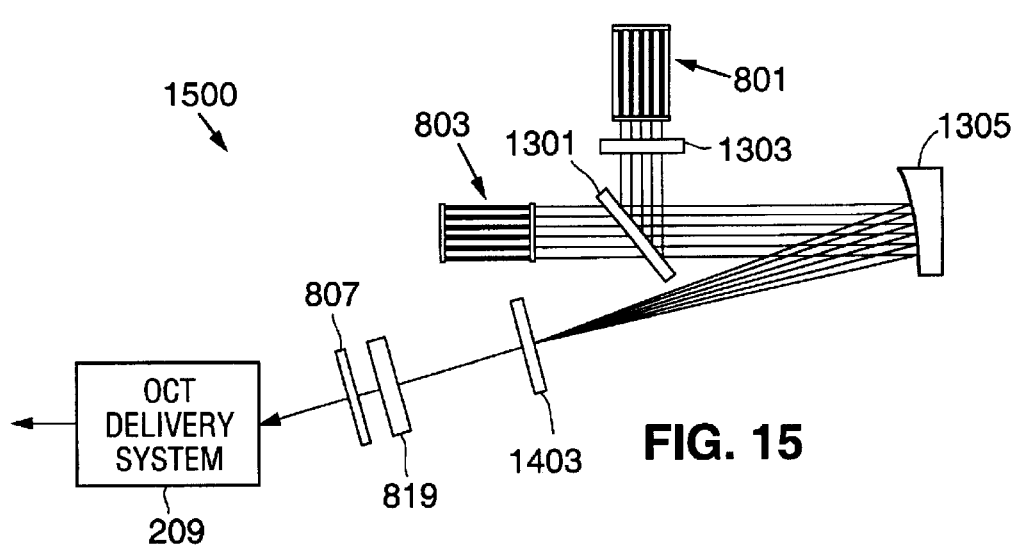
FIG. 15 is an illustration of an OCT laser system utilizing polarization multiplexing, a reflective collimating element, and a transmissive diffraction grating.
Figure 16:
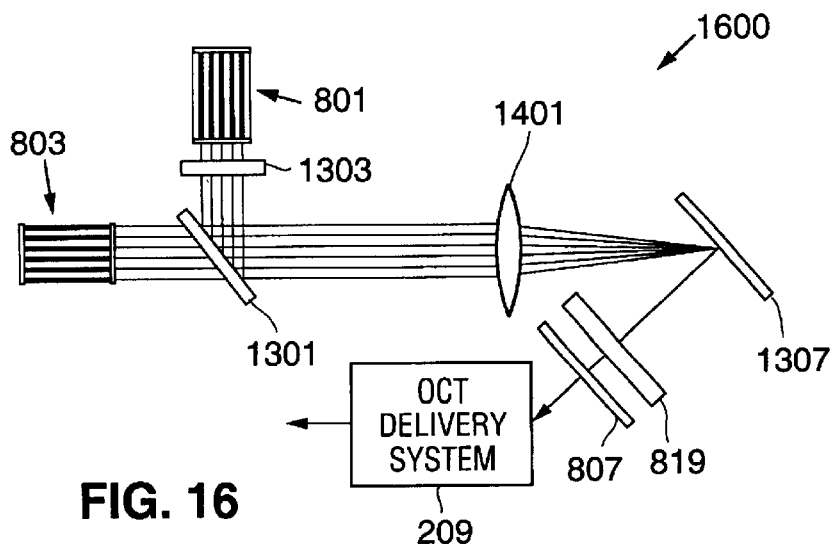
FIG. 16 is an illustration of an OCT laser system fabricated in accordance with the invention utilizing polarization multiplexing, a transmissive collimating element, and a reflective diffraction grating.
Figure 17:
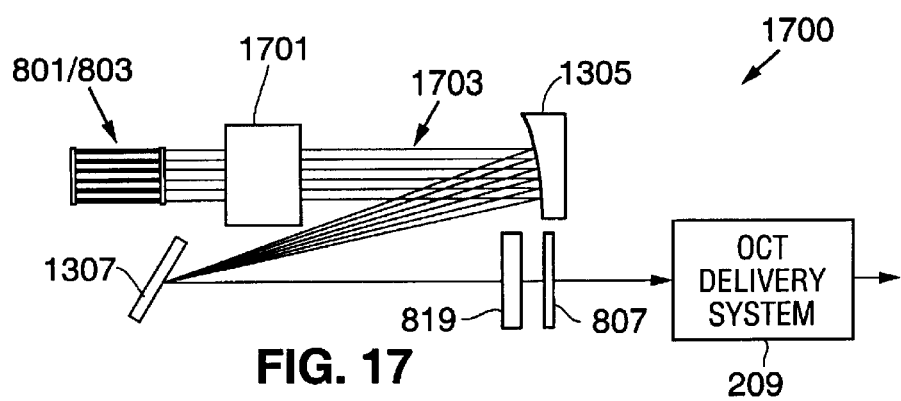
FIG. 17 is an illustration of an OCT laser system utilizing polarization multiplexing, a birefringent crystal, a reflective collimating element, and a reflective diffraction grating.
Figure 18:
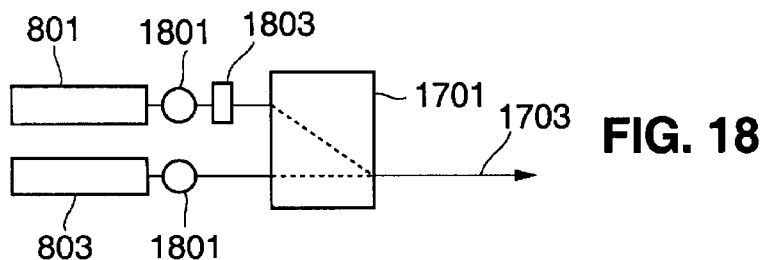
FIG. 18 is an orthogonal view of the beam combining elements of the embodiment illustrated in FIG. 17.

FIG. 17 is an illustration of an alternate embodiment of the system shown in FIG. 13, this embodiment providing a means of further reducing the size of the optical system through the use of a different array output combining technique. FIG. 18 is a cross-section of the beam combining aspects of this embodiment. In this embodiment arrays 801 and 803 are stacked one on top of the other. In order to optimize the size of the system as well as its robustness, preferably the two arrays are bonded together. The output of each array is substantially collimated by passing it through a lens element 1801, typically either a microlens array or a cylindrical rod lens. The collimated output of one of the arrays, e.g., upper array 801 in FIG. 18, then passes through a half wave plate 1803 in order to rotate the output polarization. A birefringent crystal 1701, e.g., a calcite crystal, is then used to combine the output from the two arrays into a single plane 1703. Once the beams have been combined, any of the optical configurations illustrated in FIGS. 13–16 can be used to achieve the desired output wavelength spectrum.

Figure 19:
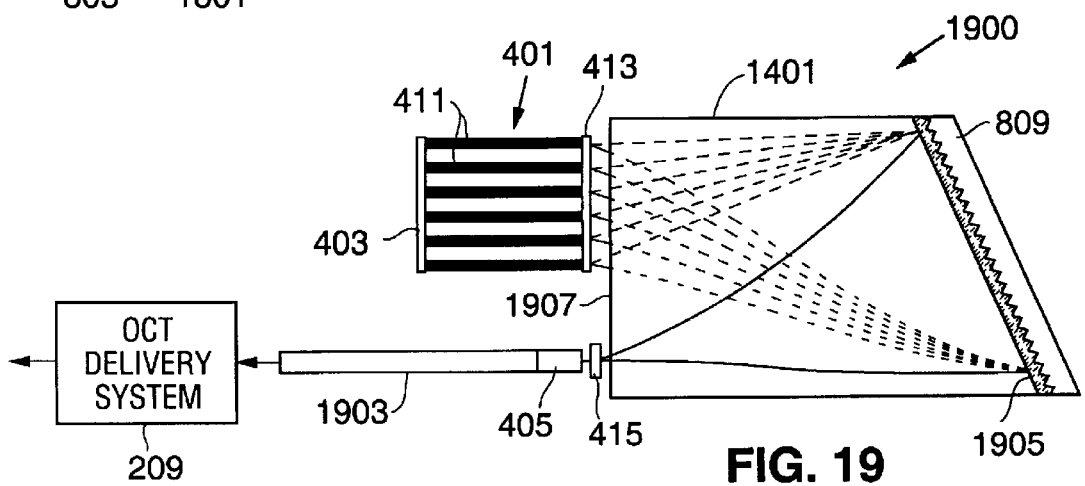
FIG. 19 is an illustration of an OCT laser system utilizing a GRIN lens.

FIG. 19 illustrates an alternate embodiment of the invention. Laser system 1900 is similar to system 400. In this embodiment, however, collimating lens 407 is replaced with a gradient index or GRIN lens 1901. Preferably output coupler 405 is directly coupled to an optical fiber 1903 which serves as the OCT delivery system. In this case output coupler 405 can be buried within fiber 1903, attached to fiber 1903 with an index matching, optically transparent adhesive, or directly deposited onto the cleaved end facet of fiber 1903. It is understood that other methods of delivering the optical energy from system 1900 to the area to be imaged can be used.

GRIN lens 1901 is approximately a ¼ pitch GRIN lens with diffraction grating 409 bonded to an end face 1905 of lens 1901 using an index matching, optically transparent adhesive. Alternately, diffraction grating 409 can be fabricated directly onto surface 1905 of GRIN lens 1901 using any of a variety of known techniques.

In a manner similar to the previous embodiments, due to the combination of GRIN lens 1901 and reflective diffraction grating 409, each gain element 411 of array 401 oscillates within its own cavity, the wavelength of which is defined by the diffraction grating, and utilizes the same output coupler, i.e., output coupler 405. As in the previous embodiments, spatial filter 415 can be interposed between output coupler 405 and the diffraction grating. Lastly, embodiments of the invention which utilize GRIN lens 1901 can also be configured to utilize external laser cavity diffractive element 421 in combination with optical element 423 to further shape the overall output spectrum as shown and described with relation to FIG. 4.

It is understood that both array 401 and output coupler 405 can be bonded directly to end face 1907 of GRIN lens 1901, thereby providing a more robust laser system.

Figure 20:
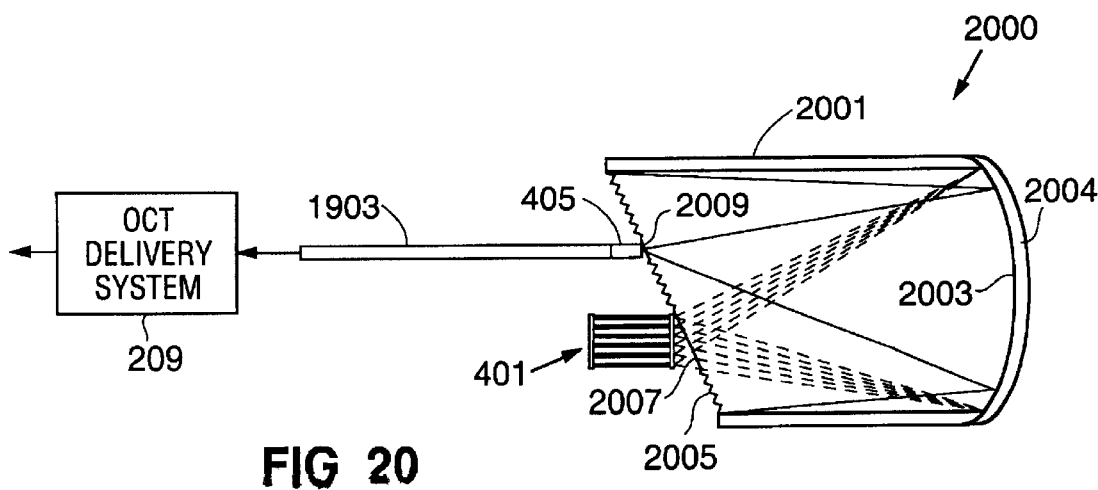
FIG. 20 is an illustration of an OCT laser system utilizing a multi-element array and a monolithic cavity design.

FIG. 20 is an illustration of another alternate embodiment of the invention. As in system 1900, system 2000 is designed to utilize a single output coupler 405 for each element 411 of an array 401 of gain elements. Preferably output coupler 405 is coupled to single mode fiber 1903, for example by burying the output coupler into the entrance aperture of the fiber. However, as opposed to GRIN lens 1901, system 2000 uses a single optic 2001 of uniform index. A shaped back surface 2003 of optic 2001 is coated with a highly reflective optical coating 2004, designed for the wavelengths of interest. In this embodiment a reflective diffraction grating 2005 is coupled to the front surface of optic 2001, grating 2005 including an entrance aperture 2007 for array 401 and an output aperture 2009 for output coupler 405. Preferably output coupler 405 is deposited directly onto the front surface of optic 2001 at aperture 2009 and fiber 1903 is coupled, for example using an index matching adhesive, to aperture 2009 and coupler 405. Preferably the front facets of array elements 411 and entrance aperture 2007 are AR coated to minimize optical losses. More preferably, array 401 is bonded directly to entrance aperture 2007, thus providing an extremely robust optical system.

As illustrated in FIG. 20, reflector 2004 on curved surface 2003 first directs the light from each array element 411 onto reflective grating 2005, and then focuses the light reflected by grating 2005 onto output coupler 405. Preferably the light from array elements 411 is substantially collimated by reflective surface 2004 onto the diffraction grating.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method of optical coherence tomography imaging, the method comprising the steps of:

multiplexing a plurality of laser beams into a single output beam, wherein said multiplexing step occurs within a single resonator cavity;

splitting said output beam into a reference beam and a sampling beam;

directing said reference beam at a reference;

translating said reference;

directing said sampling beam at a sample;

monitoring a reflected reference beam from said reference and a reflected sampling beam from said sample;

outputting a signal dependent on an amplitude and a phase corresponding to said monitored reflected reference beam and reflected sampling beam;

processing said signal to determine an image of said sample.

2. An optical coherence tomography system comprising:

a laser gain element array comprised of a plurality of laser gain elements;

a GRIN lens, wherein emissions from said plurality of laser gain elements pass through said GRIN lens;

a reflective diffraction grating, wherein emissions passing through said GRIN lens from said plurality of laser gain elements overlap on said diffraction grating and are reflected by said diffraction grating back through said GRIN lens;

an output coupler, wherein emissions from said plurality of laser gain elements reflected by said diffraction grating are focused onto said output coupler, said output coupler outputting a single output beam;

a beam splitter, said beam splitter splitting said output beam into a reference beam and a sampling beam;

a reference, wherein said reference beam impinges on said reference, said reference reflecting at least a portion of said reference beam;

a reference translation stage;

a detector, wherein said detector monitors said reflected reference beam and a reflected sampling beam, said detector outputting a signal corresponding to said monitored reflected reference beam and said reflected sampling beam; and a processor coupled to said detector, said processor processing said signal output by said detector.

3. The laser resonator cavity of claim 2, wherein said GRIN lens is a substantially ¼ pitch GRIN lens.

4. The optical coherence tomography system of claim 2, further comprising a monitor coupled to said processor, said monitor displaying an image of a sample interrogated by said sampling beam.

5. The optical coherence tomography system of claim 2, wherein said signal output by said detector is dependent on an amplitude and a phase corresponding to said monitored reflected reference beam and reflected sampling beam, wherein said phase is proportional to an optical path length difference between a sampling distance and a reference distance, said sampling distance corresponding to a distance between said beam splitter and a sample and said reference distance corresponding to a distance between said beam splitter and said reference, wherein said phase varies as said translation stage varies said reference distance, and wherein said amplitude is proportional to a reflectance of a sample region interrogated by said sampling beam.

6. An optical coherence tomography system comprising:

a plurality of individual laser sources;

means for combining a plurality of output beams corresponding to said plurality of individual laser sources into a single output beam, wherein said combining means is comprised of a plurality of beam combiners;

a beam splitter, said beam splitter splitting said output beam into a reference beam and a sampling beam;

a reference, wherein said reference beam impinges on said reference, said reference reflecting at least a portion of said reference beam;

a reference translation stage;

a detector, wherein said detector monitors said reflected reference beam and a reflected sampling beam, said detector outputting a signal corresponding to said monitored reflected reference beam and said reflected sampling beam; and a processor coupled to said detector, said processor processing said signal output by said detector.

7. An optical coherence tomography system comprising:

a plurality of individual laser sources;

means for combining a plurality of output beams corresponding to said plurality of individual laser sources into a single output beam;

a beam splitter, said beam splitter splitting said output beam into a reference beam and a sampling beam, wherein said beam splitter is a fiber splitter;

a reference, wherein said reference beam impinges on said reference, said reference reflecting at least a portion of said reference beam;

a reference translation stage;

a detector, wherein said detector monitors said reflected reference beam and a reflected sampling beam, said detector outputting a signal corresponding to said monitored reflected reference beam and said reflected sampling beam; and a processor coupled to said detector, said processor processing said signal output by said detector.

8. An optical coherence tomography system comprising:

a first laser gain element array comprised of a first plurality of laser gain elements;

a first collimating optical element, wherein emissions from said first plurality of laser gain elements are substantially collimated by said first collimating optical element;

a diffraction grating, wherein said first collimated emissions impinge on said diffraction grating;

an output coupler, said output coupler outputting a single output beam;

a beam splitter, said beam splitter splitting said output beam into a reference beam and a sampling beam;

a reference, wherein said reference beam impinges on said reference, said reference reflecting at least a portion of said reference beam;

a reference translation stage;

a detector, wherein said detector monitors said reflected reference beam and a reflected sampling beam, said detector outputting a signal corresponding to said monitored reflected reference beam and said reflected sampling beam; and a processor coupled to said detector, said processor processing said signal output by said detector.

9. The optical coherence tomography system of claim 8, wherein said first laser gain element array is selected from the group of arrays consisting of semiconductor diode laser arrays, side pumped solid state laser materials, end pumped solid state laser materials, and fiber laser arrays.

10. The optical coherence tomography system of claim 8, wherein said first laser gain element array is comprised of a plurality of index guided arrays, each of said plurality of index guided arrays having a distinct center wavelength.

11. The optical coherence tomography system of claim 8, wherein said first laser gain element array is comprised of a single array with a laterally varying quantum well thickness.

12. The optical coherence tomography system of claim 8, wherein said first laser gain element array is comprised of a single array with a laterally varying epitaxy.

13. The optical coherence tomography system of claim 8, wherein said first collimating optical element is selected from the group of collimating optical elements consisting of reflective collimating optical elements and transmissive collimating optical elements.

14. The optical coherence tomography system of claim 8, wherein said diffraction grating is selected from the group of diffraction gratings consisting of reflective diffraction gratings and transmissive diffraction gratings.

15. The optical coherence tomography system of claim 8, further comprising a spatial filter.

16. The optical coherence tomography system of claim 15, wherein said spatial filter is interposed between said diffraction grating and said output coupler.

17. The optical coherence tomography system of claim 8, further comprising a microlens array interposed between said first laser gain element array and said first collimating optical element.

18. The optical coherence tomography system of claim 8, further comprising:
   a second laser gain element array comprised of a second plurality of laser gain elements; and
   a second collimating optical element, wherein emissions from said second plurality of laser gain elements are substantially collimated by said second collimating optical element, and wherein said first and second collimated emissions overlap on said diffraction grating.

19. The optical coherence tomography system of claim 18, wherein a first laser gain element of said first laser gain element array resonates wavelengths from $\lambda$ to $\lambda+\Delta\lambda$, wherein a second laser gain element of said first laser gain element array resonates wavelengths from $\lambda+2\Delta\lambda$ to $\lambda+3\Delta\lambda$, wherein a $n^{th}$ laser gain element of said first laser gain element array resonates wavelengths from $\lambda+(2n-2)\Delta\lambda$ to $\lambda+(2n-1)\Delta\lambda$, wherein a first laser gain element of said second laser gain element array resonates wavelengths from $\lambda+\Delta\lambda$ to $\lambda+2\Delta\lambda$, wherein a second laser gain element of said second laser gain element array resonates wavelengths from $\lambda+3\Delta\lambda$ to $\lambda+4\Delta\lambda$, and wherein a $n^{th}$ laser gain element of said second laser gain element array resonates wavelengths from $\lambda+(2n-1)\Delta\lambda$ to $\lambda+(2n)\Delta\lambda$.

20. The optical coherence tomography system of claim 18, said first laser gain element array has a 50 percent duty cycle, and wherein said second laser gain element array has a 50 percent duty cycle.

21. The optical coherence tomography system of claim 8, further comprising a monitor coupled to said processor, said monitor displaying an image of a sample interrogated by said sampling beam.

22. The optical coherence tomography system of claim 8, wherein said signal output by said detector is dependent on an amplitude and a phase corresponding to said monitored reflected reference beam and reflected sampling beam.

23. The optical coherence tomography system of claim 22, wherein said phase is proportional to an optical path length difference between a sampling distance and a reference distance, said sampling distance corresponding to a distance between said beam splitter and a sample and said reference distance corresponding to a distance between said beam splitter and said reference, wherein said phase varies as said translation stage varies said reference distance.

24. The optical coherence tomography system of claim 22, wherein said amplitude is proportional to a reflectance of a sample region interrogated by said sampling beam.

25. The optical coherence tomography system of claim 8, wherein said beam splitter is a fiber splitter.

26. An optical coherence tomography system comprising:
   a first laser gain element array comprised of a first plurality of laser gain elements;
   a second laser gain element array comprised of a second plurality of laser gain elements;
   a beam combining element, said beam combining element combining a first plurality of emissions from said first plurality of laser gain elements with a second plurality of emissions from said second plurality of laser gain elements to form a plane of combined emissions;
   a wave plate interposed between said first laser gain element array and said beam combining element;
   a collimating optical element, said collimating optical element collimating said combined emissions;
   a diffraction grating, wherein said collimated combined emissions are directed onto said diffraction grating;
   an output coupler, said output coupler outputting a single output beam;
   a beam splitter, said beam splitter splitting said output beam into a reference beam and a sampling beam;
   a reference, wherein said reference beam impinges on said reference, said reference reflecting at least a portion of said reference beam;
   a reference translation stage;
   a detector, wherein said detector monitors said reflected reference beam and a reflected sampling beam, said detector outputting a signal corresponding to said monitored reflected reference beam and said reflected sampling beam; and
   a processor coupled to said detector, said processor processing said signal output by said detector.

27. The optical coherence tomography system of claim 26, wherein said beam combining element is a thin film polarizer.

28. The optical coherence tomography system of claim 26, further comprising:
   a first lens element proximate to said first laser gain element array, said first lens element reducing divergence of said first plurality of emissions of said first laser gain element array along at least a first axis; and
   a second lens element proximate to said second laser gain element array, said second lens element reducing divergence of emissions of said second laser gain element array along at least said first axis.

29. The optical coherence tomography system of claim 28, wherein said first lens element is a first cylindrical lens and said second lens element is a second cylindrical lens.

30. The optical coherence tomography system of claim 26, wherein said beam combining element is a birefringent crystal.

31. The optical coherence tomography system of claim 30, further comprising:
   a first lens element proximate to said first laser gain element array, said first lens element reducing divergence of said first plurality of emissions of said first laser gain element array along at least a first axis; and a second lens element proximate to said second laser gain element array, said second lens element reducing divergence of emissions of said second laser gain element array along at least said first axis.

32. The optical coherence tomography system of claim 31, wherein said first lens element is a first cylindrical lens and said second lens element is a second cylindrical lens.

33. The optical coherence tomography system of claim 26, wherein said first laser gain element array is selected from the group of arrays consisting of semiconductor diode laser arrays, side pumped solid state laser materials, end pumped solid state laser materials, and fiber laser arrays, and wherein said second laser gain element array is selected from the group of arrays consisting of semiconductor diode laser arrays, side pumped solid state laser materials, end pumped solid state laser materials, and fiber laser arrays.

34. The optical coherence tomography system of claim 26, wherein said first laser gain element array is comprised of a first plurality of index guided arrays, each of said first plurality of index guided arrays having a distinct center wavelength, and wherein said second laser gain element array is comprised of a second plurality of index guided arrays, each of said second plurality of index guided arrays having a distinct center wavelength.

35. The optical coherence tomography system of claim 26, wherein said first laser gain element array is comprised of a first single array with a laterally varying quantum well thickness, and wherein said second laser gain element array is comprised of a second single array with a laterally varying quantum well thickness.

36. The optical coherence tomography system of claim 26, wherein said first laser gain element array is comprised of a first single array with a laterally varying epitaxy, and wherein said second laser gain element array is comprised of a second single array with a laterally varying epitaxy.

37. The optical coherence tomography system of claim 26, wherein said collimating optical element is selected from the group of collimating optical elements consisting of reflective collimating optical elements and transmissive collimating optical elements.

38. The optical coherence tomography system of claim 26, wherein said diffraction grating is selected from the group of diffraction gratings consisting of reflective diffraction gratings and transmissive diffraction gratings.

39. The optical coherence tomography system of claim 26, further comprising a spatial filter.

40. The optical coherence tomography system of claim 39, wherein said spatial filter is interposed between said diffraction grating and said output coupler.

41. The optical coherence tomography system of claim 26, wherein a first laser gain element of said first laser gain element array resonates wavelengths from $\lambda$ to $\lambda+\Delta\lambda$, wherein a second laser gain element of said first laser gain element array resonates wavelengths from $\lambda+2\Delta\lambda$ to $\lambda+3\Delta\lambda$, wherein a $n^{th}$ laser gain element of said first laser gain element array resonates wavelengths from $\lambda+(2n-2)\Delta\lambda$ to $\lambda+(2n-1)\Delta\lambda$, wherein a first laser gain element of said second laser gain element array resonates wavelengths from $\lambda+\Delta\lambda$ to $\lambda+2\Delta\lambda$, wherein a second laser gain element of said second laser gain element array resonates wavelengths from $\lambda+3\Delta\lambda$ to $\lambda+4\Delta\lambda$, and wherein a $n^{th}$ laser gain element of said second laser gain element array resonates wavelengths from $\lambda+(2n-1)\Delta\lambda$ to $\lambda+(2n)\Delta\lambda$.

42. The optical coherence tomography system of claim 26, said first laser gain element array has a 50 percent duty cycle, and wherein said second laser gain element array has a 50 percent duty cycle.

43. The optical coherence tomography system of claim 26, further comprising a monitor coupled to said processor, said monitor displaying an image of a sample interrogated by said sampling beam.

44. The optical coherence tomography system of claim 26, wherein said signal output by said detector is dependent on an amplitude and a phase corresponding to said monitored reflected reference beam and reflected sampling beam.

45. The optical coherence tomography system of claim 44, wherein said phase is proportional to an optical path length difference between a sampling distance and a reference distance, said sampling distance corresponding to a distance between said beam splitter and a sample and said reference distance corresponding to a distance between said beam splitter and said reference, wherein said phase varies as said translation stage varies said reference distance.

46. The optical coherence tomography system of claim 44, wherein said amplitude is proportional to a reflectance of a sample region interrogated by said sampling beam.

47. The optical coherence tomography system of claim 26, wherein said beam splitter is a fiber splitter.

48. An optical coherence tomography system comprising:
a laser gain element array comprised of a plurality of laser gain elements;
an optical element of a uniform optical index, wherein emissions from said plurality of laser gain elements pass through an entrance aperture on a leading surface of said optical element;
a reflective coating coupled to a shaped back surface of said optical element, wherein said reflective coating on said shaped back surface substantially collimates said emissions from said plurality of laser gain elements;
a reflective diffraction grating coupled to said leading surface of said optical element, wherein said substantially collimated emissions from said plurality of laser gain elements are reflected by said diffraction grating back through said optical element, wherein said reflective coating on said shaped back surface substantially focuses said emissions from said plurality of laser gain elements reflected by said diffraction grating, wherein said focussed emissions pass through an exit aperture on said leading surface of said optical element;
an output coupler proximate to said exit aperture, wherein emissions from said plurality of laser gain elements focussed by said reflective coating on said shaped back surface are focused onto said output coupler, said output coupler outputting a single output beam;
a beam splitter, said beam splitter splitting said output beam into a reference beam and a sampling beam;
a reference, wherein said reference beam impinges on said reference, said reference reflecting at least a portion of said reference beam;
a reference translation stage;
a detector, wherein said detector monitors said reflected reference beam and a reflected sampling beam, said detector outputting a signal corresponding to said monitored reflected reference beam and said reflected sampling beam; and
a processor coupled to said detector, said processor processing said signal output by said detector.

49. The optical coherence tomography system of claim 48, further comprising a monitor coupled to said processor, said monitor displaying an image of a sample interrogated by said sampling beam.

50. The optical coherence tomography system of claim 48, wherein said signal output by said detector is dependent on an amplitude and a phase corresponding to said monitored reflected reference beam and reflected sampling beam, wherein said phase is proportional to an optical path length difference between a sampling distance and a reference distance, said sampling distance corresponding to a distance between said beam splitter and a sample and said reference distance corresponding to a distance between said beam splitter and said reference, wherein said phase varies as said translation stage varies said reference distance, and wherein said amplitude is proportional to a reflectance of a sample region interrogated by said sampling beam.

* * * * *